(12) United States Patent
O'Connor et al.

(10) Patent No.: US 11,274,283 B2
(45) Date of Patent: Mar. 15, 2022

(54) METHOD FOR THE ENZYMATIC CONVERSION OF A PHENOL SUBSTRATE INTO A CORRESPONDING CATECHOL PRODUCT

(71) Applicant: University College Dublin, National University of Ireland, Dublin, Dublin (IE)

(72) Inventors: Kevin O'Connor, Dublin (IE); Susan Molloy, Dublin (IE); Reeta Davis, Dublin (IE); Wesley Shaw, Dublin (IE)

(73) Assignee: University College Dublin, National University of Ireland, Dublin, Dublin (IE)

( * ) Notice: Subject to any disclaimer, the term of this patent is extended or adjusted under 35 U.S.C. 154(b) by 0 days.

(21) Appl. No.: 17/029,629

(22) Filed: Sep. 23, 2020

(65) Prior Publication Data

US 2021/0062164 A1  Mar. 4, 2021

Related U.S. Application Data

(62) Division of application No. 15/536,534, filed as application No. PCT/EP2015/079177 on Dec. 9, 2015, now Pat. No. 10,822,594.

(30) Foreign Application Priority Data

Dec. 17, 2014 (GB) .................................. 1422508

(51) Int. Cl.
*C12P 7/22* (2006.01)
*C12N 9/02* (2006.01)
*C07C 39/11* (2006.01)
*C12Q 1/26* (2006.01)

(52) U.S. Cl.
CPC ............ *C12N 9/0071* (2013.01); *C07C 39/11* (2013.01); *C12P 7/22* (2013.01); *C12Q 1/26* (2013.01); *C12Y 114/18001* (2013.01)

(58) Field of Classification Search
CPC ........................................................ C12P 7/22
See application file for complete search history.

(56) References Cited

FOREIGN PATENT DOCUMENTS

EP    1310562    5/2003

OTHER PUBLICATIONS

Brooks et al "Biotransformation of Halpphenols Using Crude Cell Extracts of *Pseudomonasputida* F6" Applied Microbiology and Biotechnology vol. 64, pp. 486-492, 2004.
Brooks et al "Tyrosol to Hyroxytyrosol Biotransformation by Immobilized Cell Extracts of *Pseudomonasputida* F6" Enzyme and Microbial Technology vol. 39, pp. 191-196, 2006.
Espin et al "Synthesis of the Antioxidant Hydroxytyrosol Using Yrosinase as Biocatalyst" Journal of Agricultural and Food Chemistry vol. 49, pp. 1187-1193, 2001.
Fairhed et al "Bacterial Tyrosinases: Old Enzymes with New Relevance to Biotechnology" New Biotechnology vol. 2, pp. 183-191, 2012.
Hernandez-Romero et al "Polyphenol Oxidase Activity Expression in *Ralstonia solanacearum*" Applied and Environmental Microbiology vol. 71, pp. 6808-6815, 2005.
Molloy et al. "Engineering of a Bacterial Tyrosinase for Improved Catalytic Efficiency Towards D-Tyrosine Using Random and Site Directed Mutagenesis Approaches" Biotechnology and Bioengineering vol. 110, pp. 1849-1857, 2013.
Sigma Catalog Entries for Ascorbic Acid, 2000.

*Primary Examiner* — Tekchand Saidha
(74) *Attorney, Agent, or Firm* — Cesari & McKenna, LLP

(57) ABSTRACT

A method for the enzymatic conversion of a phenol substrate into a corresponding catechol product comprises the step of incubating the phenol substrate with a *Ralstonia solanacearum* tyrosinase enzyme, or a functional derivative thereof, in a reaction mixture, for a period of time sufficient to allow the enzyme convert at least some of the phenol substrate into the catechol product.

13 Claims, 5 Drawing Sheets

Figure 1:
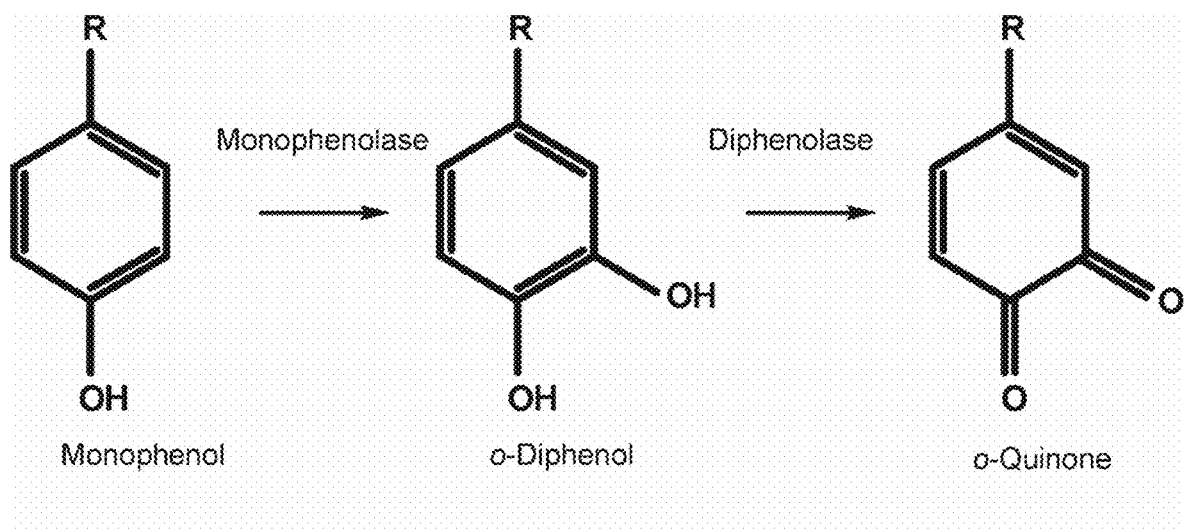

Specification includes a Sequence Listing.

SEQUENCE LISTING

```
<160> NUMBER OF SEQ ID NOS: 2

<210> SEQ ID NO 1
<211> LENGTH: 496
<212> TYPE: PRT
<213> ORGANISM: Ralstonia solanacearum

<400> SEQUENCE: 1

Met Val Val Arg Arg Thr Val Leu Lys Ala Ile Ala Gly Thr Ser Val
1               5                   10                  15

Ala Thr Val Phe Ala Gly Lys Leu Thr Gly Leu Ser Ala Val Ala Ala
            20                  25                  30

Asp Ala Ala Pro Leu Arg Val Arg Arg Asn Leu His Gly Met Lys Met
        35                  40                  45

Asp Asp Pro Asp Leu Ser Ala Tyr Arg Glu Phe Val Gly Ile Met Lys
    50                  55                  60
```

-continued

```
Gly Lys Asp Gln Thr Gln Ala Leu Ser Trp Leu Gly Phe Ala Asn Gln
 65                  70                  75                  80

His Gly Thr Leu Asn Gly Gly Tyr Lys Tyr Cys Pro His Gly Asp Trp
                 85                  90                  95

Tyr Phe Leu Pro Trp His Arg Gly Phe Val Leu Met Tyr Glu Arg Ala
            100                 105                 110

Val Ala Ala Leu Thr Gly Tyr Lys Thr Phe Ala Met Pro Tyr Trp Asn
            115                 120                 125

Trp Thr Glu Asp Arg Leu Leu Pro Glu Ala Phe Thr Ala Lys Thr Tyr
        130                 135                 140

Asn Gly Lys Thr Asn Pro Leu Tyr Val Pro Asn Arg Asn Glu Leu Thr
145                 150                 155                 160

Gly Pro Tyr Ala Leu Thr Asp Ala Ile Val Gly Gln Lys Glu Val Met
                165                 170                 175

Asp Lys Ile Tyr Ala Glu Thr Asn Phe Glu Val Phe Gly Thr Ser Arg
            180                 185                 190

Ser Val Asp Arg Ser Val Arg Pro Pro Leu Val Gln Asn Ser Leu Asp
        195                 200                 205

Pro Lys Trp Val Pro Met Gly Gly Asn Gln Gly Ile Leu Glu Arg
        210                 215                 220

Thr Pro His Asn Thr Val His Asn Asn Ile Gly Ala Phe Met Pro Thr
225                 230                 235                 240

Ala Ala Ser Pro Arg Asp Pro Val Phe Met Met His His Gly Asn Ile
                245                 250                 255

Asp Arg Val Trp Ala Thr Trp Asn Ala Leu Gly Arg Lys Asn Ser Thr
            260                 265                 270

Asp Pro Leu Trp Leu Gly Met Lys Phe Pro Asn Asn Tyr Ile Asp Pro
        275                 280                 285

Gln Gly Arg Tyr Tyr Thr Gln Gly Val Ser Asp Leu Leu Ser Thr Glu
        290                 295                 300

Ala Leu Gly Tyr Arg Tyr Asp Val Met Pro Arg Ala Asp Asn Lys Val
305                 310                 315                 320

Val Asn Asn Ala Arg Ala Glu His Leu Leu Ala Leu Phe Lys Thr Gly
                325                 330                 335

Asp Ser Val Lys Leu Ala Asp His Ile Arg Leu Arg Ser Val Leu Lys
            340                 345                 350

Gly Glu His Pro Val Ala Thr Ala Val Glu Pro Leu Asn Ser Ala Val
        355                 360                 365

Gln Phe Glu Ala Gly Thr Val Thr Gly Ala Leu Gly Ala Asp Val Gly
        370                 375                 380

Thr Gly Ser Thr Thr Glu Val Val Ala Leu Ile Lys Asn Ile Arg Ile
385                 390                 395                 400

Pro Tyr Asn Val Ile Ser Ile Arg Val Phe Val Asn Leu Pro Asn Ala
                405                 410                 415

Asn Leu Asp Val Pro Glu Thr Asp Pro His Phe Val Thr Ser Leu Ser
            420                 425                 430

Phe Leu Thr His Ala Ala Gly His Asp His His Ala Leu Pro Ser Thr
        435                 440                 445

Met Val Asn Leu Thr Asp Thr Leu Lys Ala Leu Asn Ile Arg Asp Asp
        450                 455                 460

Asn Phe Ser Ile Asn Leu Val Ala Val Pro Gln Pro Gly Val Ala Val
465                 470                 475                 480

Glu Ser Ser Gly Gly Val Thr Pro Glu Ser Ile Glu Val Ala Val Ile
```

-continued

```
               485                 490                 495

<210> SEQ ID NO 2
<211> LENGTH: 1491
<212> TYPE: DNA
<213> ORGANISM: Ralstonia solanacearum

<400> SEQUENCE: 2
tcaaatgacg gcgacctcga tcgattcggg cgtcacgccg ccgctgctct ccacggcaac      60
gccgggttgg ggtacggcca ccaggttgat cgaaaagttg tcgtcccgga tgttgagcgc     120
cttcagcgtg tcggtcaggt tcaccatggt cgacggcagg gcatggtggt cgtgtcccgc     180
cgcatgcgtc aggaagctga gcgaggtgac gaagtgcggg tcggtttccg gcacatcgag     240
gttggcgttc ggcaggttga cgaagacccg gatgctgatc acgttgtagg ggatcctgat     300
gttcttgatc agggccacga cttcggtggt actgccggta ccaacatcgg cacccagggc     360
acccgtcacg gtgccggcct cgaactggac ggcgctgttg agcggttcga ccgccgtggc     420
aaccggatgt tccccccttca gcacgctgcg cagccggata tgatcggcca gcttgacgct     480
gtcgccggtc ttgaacaggg ccagcagatg ctcggcacgg gcgttgttca ccaccttgtt     540
gtcggcgcgc ggcatgacgt catagcggta gcccagcgcc tcggtgctca gcagatcgct     600
cacgccttgc gtgtagtacc ggccctgcgg atcgatgtag ttgttgggga acttcatgcc     660
cagccacagc gggtcagtcg agttcttgcg gcccagcgcg ttccaggtgg cccatacccg     720
gtcgatattg ccgtggtgca tcatgaacac cgggtcgcgc ggcgaggcgg cggtgggcat     780
gaaggcgccg atgttgttgt ggacggtgtt gtgcggcgtg cgctccagga tgccctggtt     840
gccgcctccc atcggcaccc atttggggtc gaggctgttc tgtaccagcg gcggccggac     900
cgagcggtcg accgaacggc tggtgccgaa gacttcgaag ttggtttcgg catagatctt     960
gtccatgacc tccttctggc cgacgatggc gtcggtgagc gcgtaggggc cggtcagctc    1020
attccggttg ggcacgtaga gcgggttcgt cttgccgttg taggtcttgg cggtgaaggc    1080
ttcgggcagc aggcggtctt cggtccagtt ccagtacggc atggcgaagg tcttgtagcc    1140
ggtgagcgcg gccacggcgc gctcgtacat cagcacgaag ccgcggtgcc agggcaggaa    1200
gtaccagtcg ccgtgcgggc agtacttgta gccgccgttg agcgtaccgt gctggttggc    1260
aaagccgagc cagctcagcg cctgcgtctg gtccttgcct ttcatgatgc cgacgaactc    1320
gcgataggcc gacaggtccg ggtcgtccat cttcatgcca tgcaggttgc gccgcacgcg    1380
cagcggggcg gcatcggccg caacagcgga gaggccggtc agcttgcccg cgaataccgt    1440
ggcgacactt gtcccggcga ttgccttcag caccgttcta cgcacgacca t             1491
```

METHOD FOR THE ENZYMATIC CONVERSION OF A PHENOL SUBSTRATE INTO A CORRESPONDING CATECHOL PRODUCT

CROSS-REFERENCE TO RELATED APPLICATIONS

The present application is a divisional of commonly assigned U.S. patent application Ser. No. 15/536,534, filed on Jun. 15, 2017, now U.S. Pat. No. 10,822,594, which is the National Stage of International Application No. PCT/EP2015/079177, filed on Dec. 9, 2015, which claims the benefit of Great Britain Application No. 1422508.0, filed on Dec. 17, 2014. The contents of all prior applications are hereby incorporated by reference in their entirety.

BACKGROUND

Tyrosinase is a type of polyphenol oxidase enzyme widely distributed in nature and has several biological functions and biotechnological applications. In the presence of molecular oxygen, tyrosinase catalyses two types of reaction: the hydroxylation of monophenols to o-diphenols (monophenolase activity) and the subsequent oxidation of o-diphenols to o-quinones (diphenolase activity). The reactive quinones autopolymerize (non-enzymatically) to the macromolecular melanins which are responsible for skin and hair pigmentation, browning of fruit and wound healing in plants and arthropods. Tyrosinase has broad substrate specificity and can accept many types of phenols and diphenols (catechols). Among the substituted phenols it can act on 3- and 4-substituted phenols but 2-substituted phenols are competitive inhibitors of the enzyme.

The ability of tyrosinases to convert monophenols into o-diphenols has motivated studies regarding the production of various o-diphenols which are important precursors for the synthesis of pharmaceuticals, agrochemicals, flavours, polymerization inhibitors, inks, and antioxidants. Halocatechols are interesting synthons due to their biological activity as well as a variety of cross-coupling and halogen-metal exchange reactions starting from halocatechol intermediates to enable the synthesis of functionalized catechol building blocks. For example, fluorocatechol is potentially a valuable precursor for synthesis of pharmaceuticals, such as the adrenergic catecholamines and biogenic amines. Synthesis of substituted catechol by chemical means is complicated due to the employment of aggressive reagents, severe reaction conditions and poor yield. While tyrosinase has great potential as a biological means of synthesizing these catechols, the use of tyrosinases for catechol synthesis has been limited due to the low ratio of monophenolase to diphenolase activity where the accumulation of catechols is not favoured.

Hydroxytyrosol is a highly desired antioxidant used in food, cosmetics, and medicine. The European Food Safety Authority released a statement in 2011 supporting certain claims made about the health benefits of hydroxytyrosol. The price of hydroxytyrosol is high due to a difficult production process (e.g. extraction from olive leaves, chemical synthesis, and extraction from olive oil mill wastewater). The purity of the majority of hydroxytyrosol containing product is low (<80% and often less than 30%) with phenolics and other contaminants present. The low quality, high cost is limiting the application of hydroxytyrosol. The use of a biocatalyst such as tyrosinase would allow for high quality hydroxytyrosol.

A chemical process for production of hydroxytyrosol from tyrosol has been reported but with only 50% conversion at 6 mM concentration (EP1623960). Whole cells of *P. aeruginosa* can transform tyrosol to hydroxytyrosol (80-96% yield at 25 mM) but produces undesired byproducts (p-hydroxyphenylacetic acid and 3,4 dihydroxyphenylacetic acid) which increases the complexity and cost of the downstream process (Allouche et al., *Appl. Environ. Microbiol.*, 2004, 70, pp 2105-2109; Bouallagui and Sayadi, *J. Agric. Food Chem.*, 2006, 54, pp 9906-9911) Furthermore *P. aeruginosa* is an opportunistic pathogen which adds cost to biological control procedures within a production facility. It is unlikely to be used to produce food additives such as hydroxytyrosol.

ES2320505 describes a process for obtaining L-DOPA from L-tyrosine using the enzyme tyrosinase NP_518485 from the bacterium *Ralstonia solanacearum*. Molloy et al (*Biotechnol. Bioeng.* 2013, 110, pp 1849-1857) describes an engineered tyrosine enzyme from *Ralstonia solanacearum* for improved catalytic efficiency towards D-tyrosine using random and site directed mutagenesis.

US2003180833 (D1) describes the bioconversion of tyrosol into hydroxytyrosol using a mushroom-derived tyrosinase enzyme. While the process provides for high yields, the reaction times were very slow, with 1g tyrosol conversion using 15 mg of mushroom tyrosinase in a one litre reaction requiring 5 h to complete the reaction. Moreover, preparations of commercial mushroom tyrosinase are inhibited above 10 g/l of tyrosol and cannot complete the reaction. Scientific literature reports inhibition of mushroom tyrosinase by ascorbic acid at 5 mM (Golan-Goldhirsh and Whitaker, *J. Agric. Food Chem.*, 1984, 32, pp 1003-1009; Marin-Zamora et al, *J. Biotechnol.*, 2009, 139, pp 163-168). The *Ralstonia solanacearum* tyrosinase can act as a biocatalyst as a whole cell, crude cell lysate or purified enzyme. The first two methods of biocatalyst preparation are easy and offer advantages over mushroom tyrosinase used in a purified preparation. It has been suggested that repeated batch system for the conversion of tyrosol (5 g/l) to hydroxytyrosol is possible (Bouallagui and Sayedi *J. Agric. Food Chem.*, 2006, 54 (26), pp 9906-9911) but yields are at 85% in a single run and biocatalyst loses 60% of its activity after 3 runs resulting in poor yields, low overall concentrations and leaving high concentrations of the substrate in the final product. Complicated downstream processing to achieve a highly pure hydroxytyrosol will thus be needed. Furthermore the repeated cycles is cumbersome. Another variation on the fed batch method claims repeated product removal with beads (Brouk and Fishman, J Mol Catal B: Enzym 84:121-127) but this resulted in low product concentration and less than 50% yield.

It is an object of the invention to overcome at least one of the above-referenced problems.

SUMMARY

Figure 2:
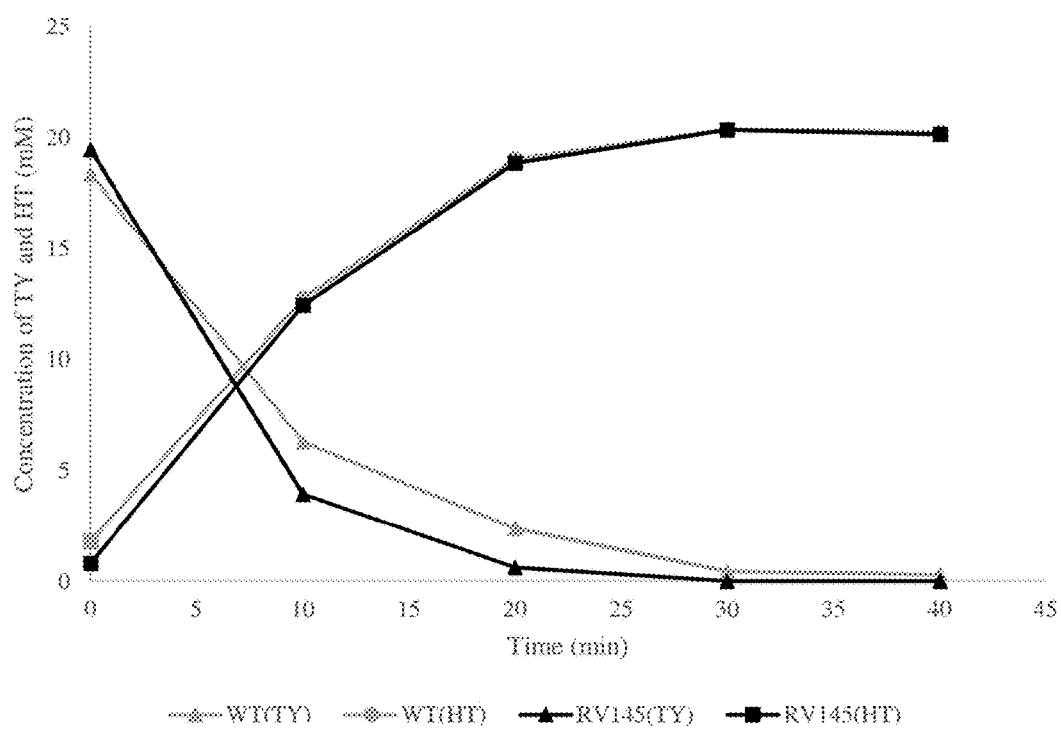
Figure 3A:
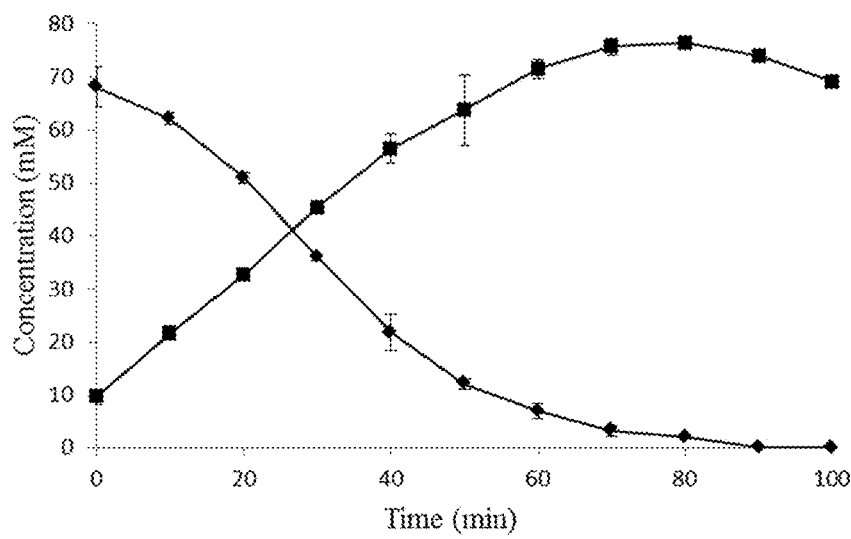
Figure 3B:
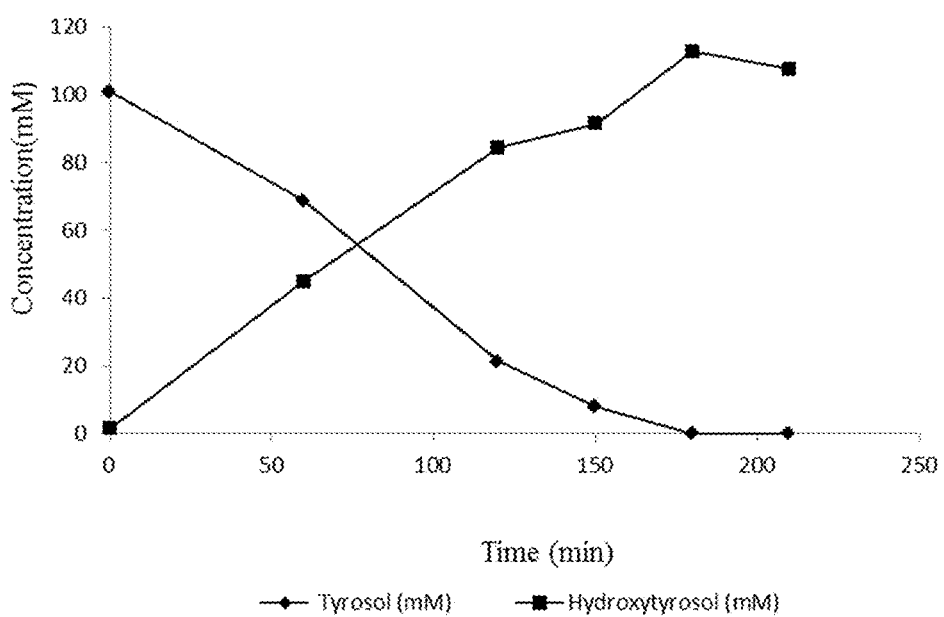
Figure 4:
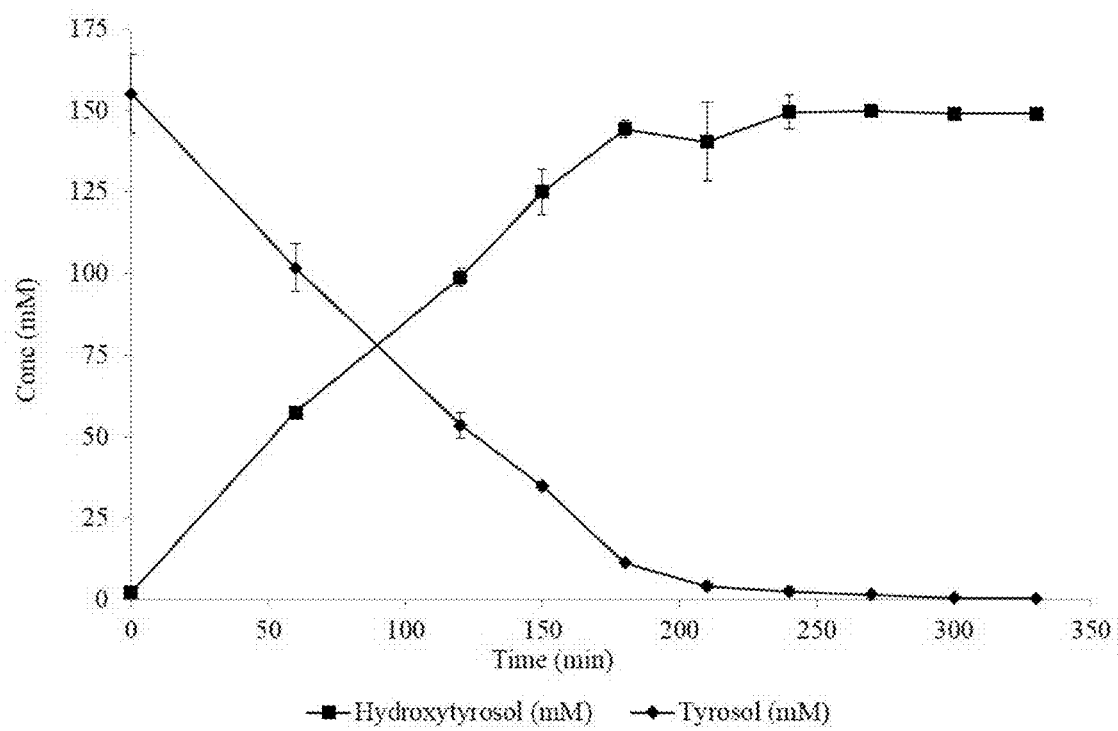
Figure 5A:
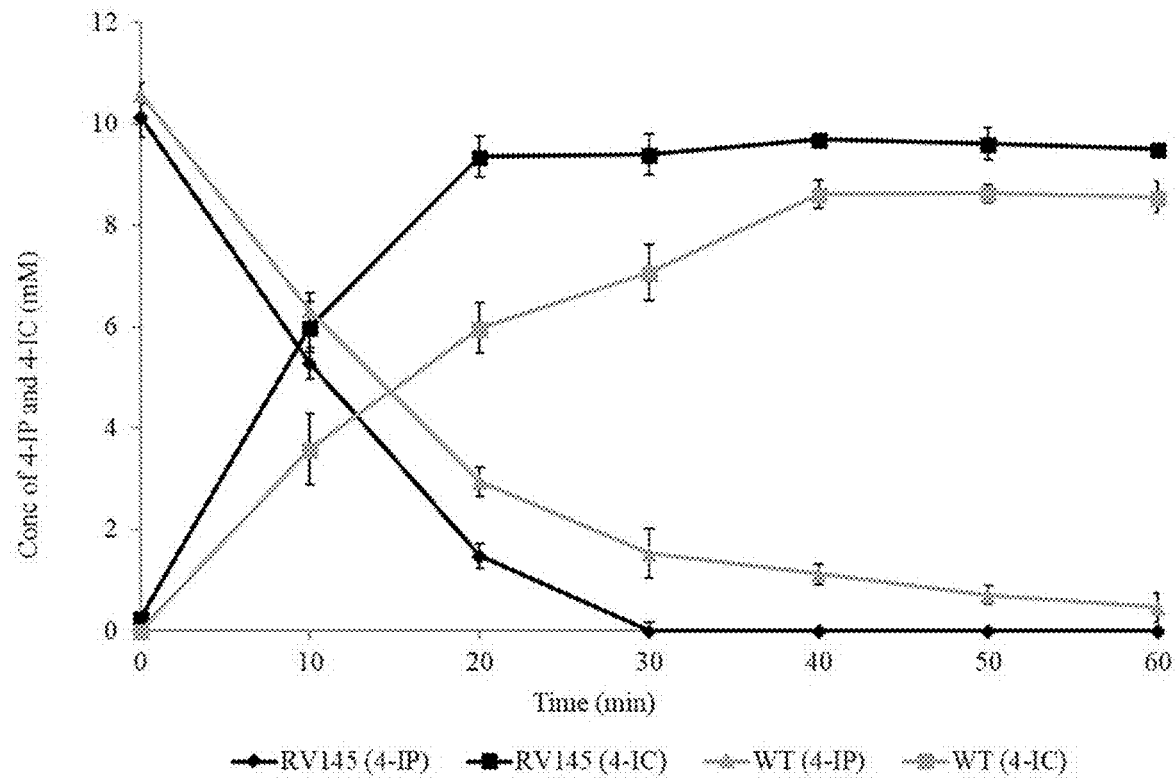
Figure 5B:
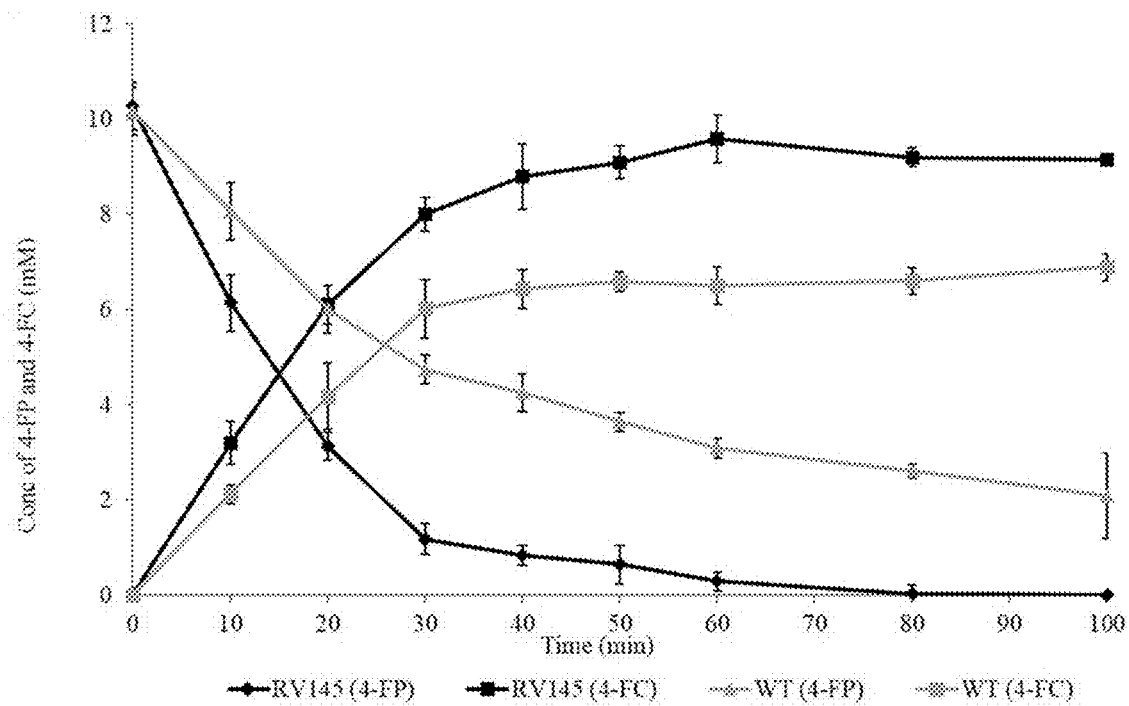
Figure 6:
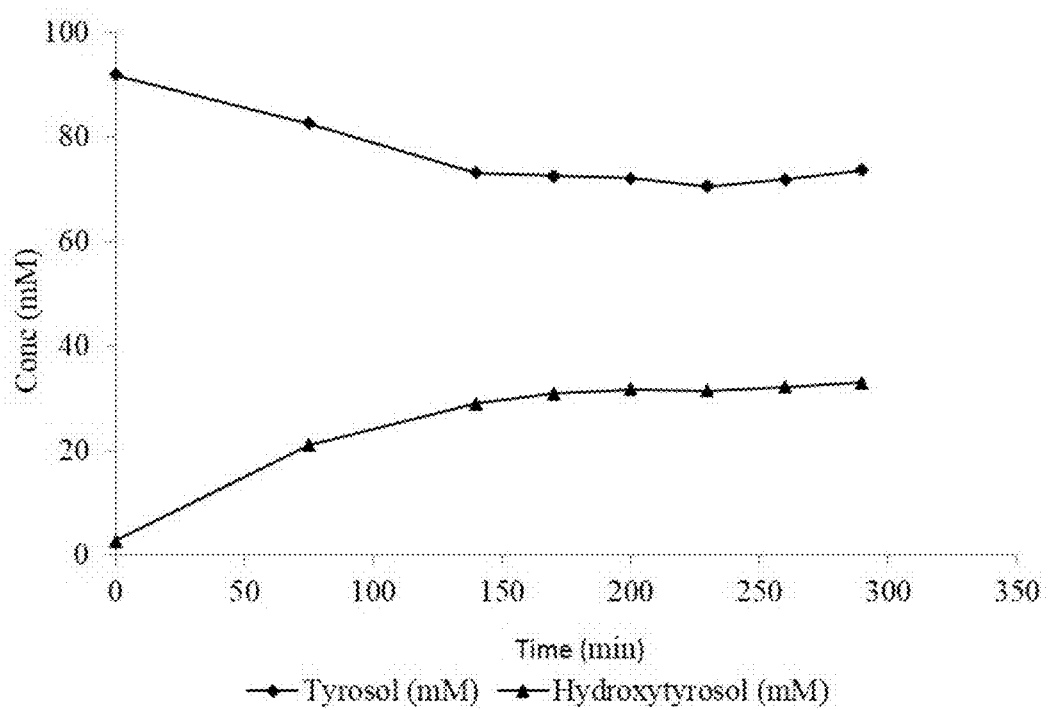

The Applicant has identified a tyrosinase enzyme from *Ralstonia solanacearum* that is capable of converting tyrosol into a hydroxytyrosol at a very high concentration (up to 150 mM and rate (up to 9.3 g/l/h), compared to any other biocatalyst (best at 25 mM and 0.4 g/l/h) (FIGS. 2-4). The conversion rates of tyrosol to corresponding catechols using *Ralstonia solanacearum* tyrosinase enzyme is far higher than the conversion rate for L-tyrosine, the natural substrate. The Applicant has also demonstrated that the *Ralstonia solanacearum* tyrosinase is capable of converting 4-halophenols into corresponding 4-halocatechols with conversion rates 4 g/l/h and product yields (>92%) that are higher than previously reported using tyrosinase or any other enzyme (FIGS. 5A and 5B). The method of the present invention requires 12.9 mg of tyrosinase from *R. solanacearum* to complete 1g tyrosol biotransformation in a one litre reaction in 20 min (15 times faster than commercial mushroom tyrosinase). Furthermore the method of the invention demonstrates reactions at high concentration of substrate that heretofore have not been achieved. The *Ralstonia solanacearum* tyrosinase demonstrates high tolerance to substrate (27.6 g/L of tyrosol) and product (30.8 g/L of hydroxytyrosol). No inhibition of *Ralstonia solanacearum* tyrosinase activity by ascorbic acid sodium salt (up to 400 mM) was observed. The *Ralstonia solanacearum* tyrosinase can act as a biocatalyst as a whole cell, crude cell lysate or purified enzyme. The first two methods of biocatalyst preparation are easy and offer advantages over mushroom tyrosianse used in a purified preparation.

Accordingly, the invention provides a method for the enzymatic conversion of a phenol substrate into a corresponding catechol product, the method comprising the steps of incubating the phenol substrate with a *Ralstonia solanacearum* tyrosinase enzyme, or a functional derivative thereof, in a reaction mixture, for a period of time sufficient to allow the enzyme convert at least some of the phenol substrate into the catechol product.

Preferably, the phenol substrate is a 3-substituted or 4-substituted phenol and the catechol product is a corresponding 3-substituted or 4-substituted catechol.

Preferably, the phenol is a hydroxyalkyl-substituted phenol. Preferably the phenol is a hydroxyethyl-substituted phenol. Preferably, the phenol is a 3- or 4-hydroxyalkyl-substituted phenol. Preferably, the phenol is a 3- or 4-hydroxyethyl-substituted phenol.

Typically, the 4-hydroxyethyl-substituted phenol is tyrosol and the 4-substituted catechol is 3,4-dihydroxyethylphenol.

Suitably, the 3-substituted or 4-substituted phenol substrate is a 3-halophenol or 4-halophenol, and the catechol product is a 3-halocatechol or 4-halocatechol.

Preferably, the reaction mixture comprises ascorbic acid. Preferably, the reaction mixture comprises 100 mM to 300 mM ascorbic acid. In one embodiment, the reaction mixture comprises up to 400 mM ascorbic acid. In one embodiment, the ascorbic acid is provided as a salt, preferably sodium ascorbate.

Suitably, the functional derivative of *Ralstonia solanacearum* tyrosinase enzyme comprises an engineered enzyme selected from the group consisting of RVC10, RV145 and C10_N322S, the details of which are described in Molloy et al., *Biotechnol. Bioeng.* 2013, 110, pp 1849-1857. In one embodiment, the functional derivative is the engineered enzyme RV145.

In one embodiment, the *Ralstonia solanacearum* tyrosinase enzyme, or functional derivative thereof, is provided as a whole cell, crude cell lysate or purified enzyme. In one embodiment, the enzyme is immobilised to a support.

Typically, the substrate concentration is at least 10 mM. In one embodiment, the substrate concentration is at least 100 mM. In one embodiment, the substrate concentration is at least 150 mM. In one embodiment, the substrate concentration is at least 175 mM.

Suitably, the method involves a step of separating catechol product from the enzyme. In one embodiment, the separation step comprises a membrane filtration step. In one embodiment, the separation step comprises a solvent extraction step. In one embodiment the separation is performed using a solid phase to bind and extract the catechol product from the aqueous biotransformation medium.

In one embodiment, the enzyme converts 90% of the phenol substrate into the catechol product. In one embodiment, the enzyme converts 100% of the phenol substrate into the catechol product.

The invention also relates to a catechol product made according to the method of the invention. In one embodiment, the catechol product is selected from hydroxytyrosol and a halocatechol. In one embodiment, the halocatechol is selected from a 3-halocatechol and a 4-halocatechol.

BRIEF DESCRIPTION OF THE DRAWINGS

FIG. 1: Hydroxylation of halophenols by the monophenolase activity and oxidation of halocatechols by the diphenolase activity of tyrosinase FIG. 2: Biotransformation of 20 mM of tyrosol in shaking flasks using WT and RV145 enzymes (20m/mL) in the presence of 40 mM ascorbic acid sodium salt (TY: tyrosol, HT: Hydroxytyrosol).

FIG. 3A: Biotransformation of 75 mM tyrosol to hydroxytyrosol by purified engineered RV145 enzyme in the presence of 150 mM ascorbic acid sodium salt.

FIG. 3B: Biotransformation of 100 mM of tyrosol using cell free lysate of *E. coli* harbouring engineered RV145 enzyme in the presence of 200 mM ascorbic acid sodium salt FIG. 4: 150 mM biotransformation of tyrosol using crude cell free lysate of *E. coli* harbouring engineered RV145 enzyme in the presence of 300 mM ascorbic acid sodium salt FIG. 5A: Biotransformation of 10 mM of 4-fluorophenol in shaking flasks using WT and RV145 enzymes (20 μg/mL) in the presence of 20 mM ascorbic acid sodium salt.

FIG. 5B: Biotransformation of 10 mM of 4-iodophenol in shaking flasks using WT and RV145 enzymes (10m/mL) in the presence of 20 mM ascorbic acid sodium salt (4-IP: 4-iodocphenol, 4-IC: 4-iodocatechol, 4-FP: 4-fluorophenol, 4-FC: 4-fluorocatechol)

FIG. 6: 100 mM biotransformation of tyrosol using commercial mushroom tyrosinase in the presence of 200 mM ascorbic acid. The reaction yields only 30% product and stops once 30 mM product is formed showing its much poorer performance compared to *R. solanacearum* tyrosinase.

DETAILED DESCRIPTION

Definitions:

"Phenol substrate" means an unsubstituted or substituted phenol, especially a 3-substituted or 4-substituted phenol. Examples of substituents include halogens or hydroxyalkyl substituents. Examples of hydroxyalkyl substituents include hydroxymethyl and hydroxyethyl substituents, especially 4-hydroxymethyl and 4-hydroxyethyl substituents. Typically, the 3-substituted or 4-substituted phenol is a 3-halophenol or 4-halophenol. Examples of halophenols include iodophenol, bromophenol, chlorophenol, and fluorophenol. Preferably, the phenol is tyrosol. Preferably, the phenol substrate is provided at a concentration up to their maximum solubility in aqueous environment. In one embodiment, the phenol substrate is selected from tyrosol, a 3-halophenol, and a 4-halophenol. In one embodiment, the phenol substrate is selected from tyrosol and a 4-halophenol.

"Corresponding catechol product" means a catechol that is produced by reacting a phenol substrate with a *Ralstonia solanacearum* tyrosinase enzyme. When the phenol substrate is a 4-halophenol (for example, 4-fluorophenol), the corresponding catechol product is the corresponding 4-fluorocatechol (4-fluorocatechol). Likewise, when the phenol substrate is 4-substituted hydroxyalkyl phenol (for example, tyrosol), the corresponding catechol product is the corresponding 4-substituted hydroxyalkyl catechol (hydroxytyrosol).

"Tyrosol" refers to 4-(2-hydroxyethyl)phenol.

"Hydroxytyrosol" means 4-(2-hydroxyethyl)-1,2-benzenediol.

"*Ralstonia solanacearum* tyrosinase enzyme" means a tyrosinease enzyme isolated from *Ralstonia solanacearum*. An example of such an enzyme is described in Molloy et al., *Biotechnol. Bioeng.* 2013, 110, pp 1849-1857. The amino acid and nucleic acid sequences for the wild-type enzyme are provided below:

*Ralstonia solanacearum* tyrosinase enzyme amino acid sequence (NP_518458)

(SEQ ID NO: 1)

```
MVVRRTVLKAIAGTSVATVFAGKLTGLSAVAADAAPLRVRRNLHGMKM
DDPDLSAYREFVGIMKGKDQTQ
ALSWLGFANQHGTLNGGYKYCPHGDWYFLPWHRGFVLMYERAVAALT
GYKTFAMPYWNWTEDRLLPEAFT
AKTYNGKTNPLYVPNRNELTGPYALTDAIVGQKEVMDKIYAETNFEVFG
TSRSVDRSVRPPLVQNSLDPK
WVPMGGGNQGILERTPHNTVHNNIGAFMPTAASPRDPVFMMHHGNIDR
VWATWNALGRKNSTDPLWLGMK
FPNNYIDPQGRYYTQGVSDLLSTEALGYRYDVMPRADNKVVNNARAEH
LLALFKTGDSVKLADHIRLRSV
LKGEHPVATAVEPLNSAVQFEAGTVTGALGADVGTGSTTEVVALIKNIRI
PYNVISIRVFVNLPNANLDV
PETDPHFVTSLSFLTHAAGHDHHALPSTMVNLTDTLKALNIRDDNFSINL
VAVPQPGVAVESSGGVTPES
IEVAVI
```

*Ralstonia solanacearum* tyrosinase enzyme nucleic acid sequence (gil30407127)

(SEQ ID NO. 2)

```
TCAAATGACGGCGACCTCGATCGATTCGGGCGTCACGCCGCCGCTGCT
CTCCACGGCAACGCCGGGTTGG
GGTACGGCCACCAGGTTGATCGAAAAGTTGTCGTCCCGGATGTTGAGC
GCCTTCAGCGTGTCGGTCAGGT
TCACCATGGTCGACGGCAGGGCATGGTGGTCGTGTCCCGCCGCATGCG
TCAGGAAGCTGAGCGAGGTGAC
GAAGTGCGGGTCGGTTTCCGGCACATCGAGGTTGGCGTTCGGCAGGTT
GACGAAGACCCGGATGCTGATC
ACGTTGTAGGGGATCCTGATGTTCTTGATCAGGGCCACGACTTCGGTG
GTACTGCCGGTACCAACATCGG
CACCCAGGGCACCCGTCACGGTGCCGGCCTCGAACTGGACGGCGCTGT
TGAGCGGTTCGACCGCCGTGGC
```

-continued

```
AACCGGATGTTCCCCCTTCAGCACGCTGCGCAGCCGGATATGATCGGC
CAGCTTGACGCTGTCGCCGGTC
TTGAACAGGGCCAGCAGATGCTCGGCACGGGCGTTGTTCACCACCTTG
TTGTCGGCGCGCGGCATGACGT
CATAGCGGTAGCCCAGCGCCTCGGTGCTCAGCAGATCGCTCACGCCTT
GCGTGTAGTACCGGCCCTGCGG
ATCGATGTAGTTGTTGGGGAACTTCATGCCCAGCCACAGCGGGTCAGT
CGAGTTCTTGCGGCCCAGCGCG
TTCCAGGTGGCCCATACCCGGTCGATATTGCCGTGGTGCATCATGAAC
ACCGGGTCGCGCGGCGAGGCGG
CGGTGGGCATGAAGGCGCCGATGTTGTTGTGGACGGTGTTGTGCGGCG
TGCGCTCCAGGATGCCCTGGTT
GCCGCCTCCCATCGGCACCCATTTGGGGTCGAGGCTGTTCTGTACCAG
CGGCGGCCGGACCGAGCGGTCG
ACCGAACGGCTGGTGCCGAAGACTTCGAAGTTGGTTTCGGCATAGATC
TTGTCCATGACCTCCTTCTGGC
CGACGATGGCGTCGGTGAGCGCGTAGGGGCCGGTCAGCTCATTCCGGT
TGGGCACGTAGAGCGGGTTCGT
CTTGCCGTTGTAGGTCTTGGCGGTGAAGGCTTCGGGCAGCAGGCGGTC
TTCGGTCCAGTTCCAGTACGGC
ATGGCGAAGGTCTTGTAGCCGGTGAGCGCGGCCACGGCGCGCTCGTA
CATCAGCACGAAGCCGCGGTGCC
AGGGCAGGAAGTACCAGTCGCCGTGCGGGCAGTACTTGTAGCCGCCG
TTGAGCGTACCGTGCTGGTTGGC
AAAGCCGAGCCAGCTCAGCGCCTGCGTCTGGTCCTTGCCTTTCATGAT
GCCGACGAACTCGCGATAGGCC
GACAGGTCCGGGTCGTCCATCTTCATGCCATGCAGGTTGCGCCGCACG
CGCAGCGGGGCGGCATCGGCCG
CAACAGCGGAGAGGCCGGTCAGCTTGCCCGCGAATACCGTGGCGACA
CTTGTCCCGGCGATTGCCTTCAG
CACCGTTCTACGCACGACCAT
```

"Functional derivative thereof" as applied to a *Ralstonia solanacearum* tyrosinase enzyme means an engineered variant of *Ralstonia solanacearum* tyrosinase enzyme that is typically capable of converting a phenol (i.e. tyrosol) into a corresponding catechol (i.e. hydroxytyrosol) at a concentration and rate that is significantly better than mushroom tyrosinease described in US2003180833 (D1). Examples of such engineered variants of *Ralstonia solanacearum* tyrosinase enzyme are described in Molloy et al (2013), including variants that are capable of converting tyrosol into hydroxytyrosol at a concentration and rate that is at least the equivalent of the wild-type *Ralstonia solanacearum* tyrosinase enzyme. In one embodiment, the engineered variant of *Ralstonia solanacearum* tyrosinase enzyme is capable of the 100% conversion of 150 mM tyrosol into hydroxytyrosol in the tyrosol biotransformation assay described below. In one embodiment, the engineered variant of *Ralstonia solanacearum* tyrosinase enzyme is capable of the 100% conversion of 175 mM tyrosol into hydroxytyrosol in the tyrosol biotransformation described below. Methods for generating and testing engineered variants of *Ralstonia solanacearum* tyrosinase enzyme will be apparent to the person skilled in the art, and are described in Molloy et al.

An "engineered variant" of the *Ralstonia solanacearum* tyrosinase enzyme protein shall be taken to mean enzymes having amino acid sequences which are substantially identical to wild-type *Ralstonia solanacearum* tyrosinase enzyme. Thus, for example, the term should be taken to include enzymes that are altered in respect of one or more amino acid residues. Preferably such alterations involve the insertion, addition, deletion and/or substitution of 5 or fewer amino acids, more preferably of 4 or fewer, even more preferably of 3 or fewer, most preferably of 1 or 2 amino acids only. Insertion, addition and substitution with natural and modified amino acids is envisaged. The engineered variant may have conservative amino acid changes, wherein the amino acid being introduced is similar structurally, chemically, or functionally to that being substituted. Generally, the variant will have at least 70% amino acid sequence homology, preferably at least 80% sequence homology, more preferably at least 90% sequence homology, and ideally at least 95%, 96%, 97%, 98% or 99% sequence homology with wild-type *Ralstonia solanacearum* tyrosinase enzyme. In this context, sequence homology comprises both sequence identity and similarity, i.e. a polypeptide sequence that shares 70% amino acid homology with wild-type *Ralstonia solanacearum* tyrosinase enzyme is one in which any 70% of aligned residues are either identical to, or conservative substitutions of, the corresponding residues in wild-type *Ralstonia solanacearum* tyrosinase enzyme. Specific variants included within the scope of the invention are the engineered variants described in (Molloy et al., 2013), especially (RVC10, RV145 and C10_N322S). In one embodiment, the engineered variant of *Ralstonia solanacearum* tyrosinase enzyme is capable of complete conversion of a tyrosol substrate to hydroxytyrosol at concentrations an order of magnitude higher than previously reported by any tyrosinase or other biocatalyst (e.g. 175 mM tyrosol)

The term "engineered variant" is also intended to include chemical derivatives of wild-type *Ralstonia solanacearum* tyrosinase enzyme, i.e. where one or more residues of the wild-type enzyme is chemically derivatized by reaction of a functional side group. Also included within the term variant are wild-type *Ralstonia solanacearum* tyrosinase enzymes in which naturally occurring amino acid residues are replaced with amino acid analogues. Examples of side chain modifications include modification of amino groups, such as by reductive alkylation by reaction with an aldehyde followed by reduction with $NaBH_4$; amidation with methylacetimidate; acetylation with acetic anhydride;

carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with $NABH_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tyrosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during enzyme synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

The following are numbered statements of invention:

1. A method for the enzymatic conversion of a phenol substrate into a corresponding catechol product, in which the phenol substrate is selected from tyrosol and a 4-halophenol, the method comprising the steps of incubating the phenol substrate with a *Ralstonia solanacearum* tyrosinase enzyme, or a functional derivative thereof, in a reaction mixture, for a period of time sufficient to allow the enzyme convert at least some of the phenol substrate into the catechol product.

2. A method according to statement 1 in which the phenol substrate is a tyrosol and the catechol product is hydroxytyrosol.

3. A method according to statement 1 in which the phenol substrate is a halophenol and the catechol product is a halocatechol.

4. A method according to any preceding statement in which the reaction mixture comprises ascorbic acid or its sodium salt 5. A method according to any preceding statement in which the reaction mixture comprises 20-350 mM ascorbic acid.

6. A method according to any preceding statement in which the functional derivative of the *Ralstonia solanacearum* tyrosinase enzyme is an engineered variant of *Ralstonia solanacearum* tyrosinase enzyme that is capable of the 100% conversion of 175 mM tyrosol into hydroxytyrosol 7. A method according to any preceding statement in which the functional derivative of *Ralstonia solanacearum* tyrosinase enzyme is an engineered enzyme selected from the group consisting of RVC10, RV145 and C10_N322S.

8. A method according to any preceding statement in which the *Ralstonia solanacearum* tyrosinase enzyme, or functional derivative thereof, is provided as an extract from a bacteria that expresses the *Ralstonia solanacearum* tyrosinase enzyme, or functional derivative thereof.

9. A method according to any of statements 1 to 7 in which the *Ralstonia solanacearum* tyrosinase enzyme, or functional derivative thereof, is provided as a bacteria that expresses the *Ralstonia solanacearum* tyrosinase enzyme, or functional derivative thereof.

10. A method according to any of statements 1 to 7 in which the *Ralstonia solanacearum* tyrosinase enzyme, or functional derivative thereof, is provided as a purified enzyme.

11. A method according to any of statements 1 to 7 in which the *Ralstonia solanacearum* tyrosinase enzyme, or functional derivative thereof, is provided as a crude mixture in the form of a cell extract.

12. A method according to any preceding statement, in which the substrate concentration is at least 75 mM.

13. A method as claimed in any preceding statement in which the catechol product is separated from impurities present in the reaction mixture by chilling the reaction mixture after the enzymatic conversion step.

14. A method as claimed in any preceding statement in which the catechol product is separated from impurities present in the reaction mixture by refrigerating or freezing the reaction mixture after the enzymatic conversion step.

EXPERIMENTAL

Materials and Methods

Strains, Growth Conditions and Purification of Tyrosinase

Recombinant *E. coli* BL21 were used to express wild type (WT) tyrosinase gene from *R. solanacearum* and three engineered variants (RV145, RVC10, C10_N322S) of the same gene previously generated by Molloy et al (2013). All strains were maintained in Lysogeny broth (LB) with 50% glycerol at −80° C. In preparation for induction and tyrosinase purification, the *E. coli* strains stored at −80° C. were streaked on LB agar and incubated at 37° C. for 24 h. The primary inoculum was cultured in a rotary shaker (200 rpm, 37° C.) in 5 mL of LB overnight. Carbenicillin (50 μg/mL) was used as the antibiotic for the maintenance of the plasmid throughout the study. Tyrosinase production was induced and the enzyme was purified as described earlier (Molloy et al. 2013). Different fractions of the purified tyrosinase were analysed by 10% SDS-PAGE for confirmation of purity and molecular weight. The protein concentration was determined by bicinchoninic acid method (Smith et al. 1985) using bovine serum albumin as the standard.

Preparation of Substrates and Other Chemicals

Various monophenol substrates such as 4-fluorophenol, 4-bromophenol, 4-chlorophenol, and 4-iodophenol were purchased from Sigma-Aldrich (Dublin, Ireland). Stock solutions (1 M) of the 4-bromophenol, and 4-iodophenol were prepared in 100% ethanol and subsequent working solutions were further diluted in 50 mM potassium phosphate buffer (pH 7). Similarly, stock solutions (500 mM) of 4-fluorophenol and 4-chlorophenol were prepared in deionized water and working stocks were prepared in 50 mM phosphate buffer. Tyrosol was purchased from TCI Europe (Belgium) and stocks were prepared in 50 mM phosphate buffer. Ascrobic acid and ascorbic acid sodium salt (AA) (used to reduce o-quinone to o-diphenol) was prepared in deionized water freshly before the biotransformation assay Biotransformation of 4-Halogenated Phenols and Tyrosol Biotransformations of halophenols into corresponding halocatechols were carried out using purified enzymes (WT and engineered variants). Various concentrations (5, 10, and 20 mM) of halophenol biotransformations were carried out in 100 mL conical flasks with a working volume of 20 mL at 30° C. and 200 rpm in a shaker incubator. Biotransformation of tyrosol to hydroxytyrosol was carried out using purified enzymes, cell free lysate or whole cells. Various concentrations (75, 100, 150 and 175 mM) of tyrosol biotransformations were carried out in 500 mL baffled conical flasks with a working volume of 100 mL at 30° C. and 200-250 rpm in a shaker incubator. An enzyme concentration of 2 μg/mL per 1 mM of substrate was tested with a substrate to sodium ascorbate ratio of 1:2. Biotransformation of 100 mM tyrosol to hydroxytyrosol was also carried out using commercial mushroom tyrosinase (Sigma, Ireland) using the above specified conditions. Samples (450 μL) were withdrawn at various time points and immediately added to 50 μL of ice-cold 1N HCl. Samples were centrifuged (12,000 g), filtered using Whatman Mini-UniPrep™ syringeless filters (0.45 μ Whatman Inc. N.J., USA), and a sample volume of 20 μL was used for all HPLC injections.

HPLC Analysis

Filtered samples were analyzed by HPLC using a 5 μm ACE 5 C18column (25 cm×4.6 mm ID; Apex Scientific, Ireland) and a Hewlett-Packard (Palo Alto, Calif., USA) HP1100 instrument equipped with an Agilent 1100 Series Diode Array Detector. The samples were isocratically eluted at 22° C. using a phosphoric acid (0.1%, v/v) and methanol mix at a flow rate of 1.0 mL/min. The ratio of phosphoric acid to methanol was 70:30 for 4-fluorophenol and 50:50 for 4-chloro-, 4-bromo-, and 4-iodophenol.

What is claimed is:

1. A method for the enzymatic conversion of 4-halophenol into 4-halocatechol, the method comprising the step of incubating the 4-halophenol with a *Ralstonia solanacearum* tyrosinase enzyme or a functional derivative thereof, in a reaction mixture for a period of time sufficient to allow the *Ralstonia solanacearum* tyrosinase enzyme to convert at least 90% of the 4-halophenol into 4-halocatechol, in which the reaction mixture comprises ascorbic acid or its sodium salt, wherein the functional derivative is an engineered variant of *Ralstonia solanacearum* tyrosinase of SEQ ID NO: 1 selected from the group consisting of Y119F, V153A, D317Y and L330V (RV145); T183I, F185Y, N322S, and T359M (RVC10); and N322S (C10_N322S).

2. The method according to claim 1 in which the reaction mixture comprises at least 10 mM of the 4-halophenol.

3. The method according to claim 1 in which the reaction mixture comprises at least 20 mM ascorbic acid.

4. The method according to claim 1 in which the functional derivative of the *Ralstonia solanacearum* tyrosinase enzyme is capable of the 98% conversion of 10 mM 4-halophenol 4-halocatechol.

5. The method according to claim 1 in which the *Ralstonia solanacearum* tyrosinase enzyme, or functional derivative thereof, is provided as an extract from a bacteria that expresses the *Ralstonia solanacearum* tyrosinase enzyme, or functional derivative thereof.

6. The method according to claim 1 in which the *Ralstonia solanacearum* tyrosinase enzyme, or functional derivative thereof, is provided as a bacteria that expresses the *Ralstonia solanacearum* tyrosinase enzyme, or functional derivative thereof.

7. The method according to claim 1 in which the *Ralstonia solanacearum* tyrosinase enzyme, or functional derivative thereof, is provided as a purified enzyme.

8. The method according to claim 1 in which the functional derivative of *Ralstonia solanacearum* tyrosinase enzyme is RV145.

9. The method according to claim 1 in which the functional derivative of *Ralstonia solanacearum* tyrosinase enzyme is RVC10.

10. The method according to claim 1 in which the functional derivative of *Ralstonia solanacearum* tyrosinase enzyme is C10_N322S.

11. The method according to claim 1 in which the *Ralstonia solanacearum* tyrosinase enzyme, or functional derivative thereof, is provided as a crude mixture in the form of a cell extract.

12. The method according to claim 1 in which the 4-halocatechol is separated from impurities present in the reaction mixture by chilling the reaction mixture after enzymatic conversion.

13. The method according to claim 1 in which the 4-halocatechol is separated from impurities present in the reaction mixture by refrigerating or freezing the reaction mixture after enzymatic conversion.

* * * * *